United States Patent [19]

Murakami et al.

[11] 4,021,434
[45] May 3, 1977

[54] SODIUM β-[2,6-DIMETHYL-3,5-BIS(ETHOXYCARBONAL)-4-(3-NITROPHENYL)-1,4-DIHYDROPYRIDINE-1-YL]ETHYL SULFATE

[75] Inventors: Masuo Murakami; Kozo Takahashi, both of Tokyo; Teruaki Ozasa, Ageo; Kazuharu Tamazawa; Ryutaro Kawai, both of Saitama; Toichi Takenaka, Tokyo; Norio Sato, Saitama, all of Japan

[73] Assignee: Yamanouchi Pharmaceutical Co., Ltd., Tokyo, Japan

[22] Filed: Aug. 21, 1975

[21] Appl. No.: 606,728

Related U.S. Application Data

[63] Continuation-in-part of Ser. No. 559,965, May 5, 1975, abandoned, which is a continuation-in-part of Ser. No. 322,848, Jan. 11, 1973, abandoned.

[30] Foreign Application Priority Data

| Jan. 22, 1972 | Japan | 47-8482 |
| Feb. 24, 1972 | Japan | 47-18495 |
| July 19, 1972 | Japan | 47-72373 |
| July 25, 1972 | Japan | 47-74373 |

[52] U.S. Cl. .............. 260/294.8 R; 260/295.5 R; 260/279 R; 424/266
[51] Int. Cl.$^2$ ..................................... C07D 213/55
[58] Field of Search ............... 260/295.5, 294.8 F, 260/294.8 G, 294.8 R, 294.8 D

[56] References Cited

UNITED STATES PATENTS

| 3,696,112 | 10/1972 | Bossert et al. | 260/294.8 F |
| 3,708,489 | 1/1973 | Rucker et al. | 260/295.5 R |
| 3,773,773 | 11/1973 | Bossert | 260/294.8 D |

Primary Examiner—Alan L. Rotman
Attorney, Agent, or Firm—Burgess Ryan and Wayne

[57] ABSTRACT

Novel 1-substituted-1, 4-dihydropyridine derivatives, particularly diethyl 1-ethoxymethyl-4-(3-nitrophenyl)-2, 6-dimethyl-1, 4-dihydropyridine-3,5-dicarboxylate are provided. The novel derivatives have cerebral vascular dilator activity with low toxicity.

1 Claim, No Drawings

SODIUM β-[2,6-DIMETHYL-3,5-BIS(ETHOXYCARBONAL)-4-(3-NITROPHENYL)-1,4-DIHYDROPYRIDINE-1-YL]ETHYL SULFATE

BACKGROUND OF THE INVENTION

This application is a continuation-in-part of our copending application Ser. No. 559,965, filed May 5, 1975, now abandoned, which is in turn a continuation-in-part application of abandoned application Ser. No. 322,848, filed Jan. 11, 1973.

1. Field of the Invention

The present invention relates to novel 1-substituted-1,4-dihydropyridine derivatives having high cerebral vascular dilator activity and showing low toxicity. The invention relates particularly to diethyl 1-ethoxymethyl-4-(3-nitrophenyl)-2,6-dimethyl-1, 4-dihydropyridine-3,5-dicarboxylate.

2. Description of the Prior Art

As a 1,4-dihydropyridine derivative, diethyl-4-(3'-nitrophenyl)-2,6-dimethyl-1,4-dihydropyridine-3,5-dicarboxylate represented by the formula

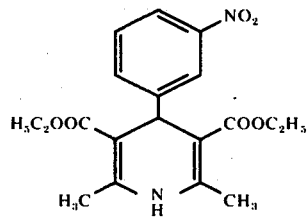

is known (see, e.g., German Patent No. 42,295 and Journal of American Chemical Society, 71, 4003–4007 (1949)). Furthermore, many other compounds are known such as 1,4-dihydropyridine derivatives (see, German OLS Nos. 1,813,436; 1,963,186; 1,963,188; 2,003,146; 2,013,431; 1,963,738; etc.).

Among the compounds practically disclosed in the specifications of those patent applications, 4-(2'-nitrophenyl)-2,6-dimethyl-1,4-dihydropyridine-3,5-dicarboxymethyl ester (Nifedipine, BAY a 1040) (* Approved name of the British Pharmacopea Commission) (see, Naturwissenschaften, 58, (11), 578 (1971) was deemed most favorable. Nifedipine has coronary vasodilator action, spasmolytic action, etc.

SUMMARY OF THE INVENTION

According to the present invention, there are provided novel 1-substituted-1,4-dihydropyridine derivatives represented by the general formula (I)

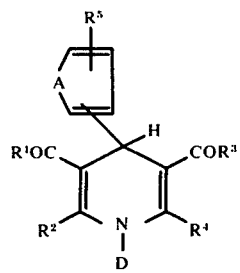

wherein $R^1$ and $R^3$, which may be the same or different, each represents a lower alkyl group or a lower alkoxy group which may have been substituted by a lower alkoxy group; $R^2$ and $R^4$, which may be the same or different, each represents a lower alkyl group, each of said $R^1$ and $R^2$ or said $R^3$ and $R^4$ may combine together to form a lower alkylene group; $R^5$ represents a hydrogen atom, a nitro group, a halogen atom, an azide group, a lower alkyl group, a lower alkoxy group, a cyano group, a lower alkylsulfonyl group, a di-lower alkylamino group, or a mono-lower alkylamino group; $R^6$ represents a lower alkyl group, a lower alkenyl group, a phenyl group, or a benzyl group; A represents —CH=CH—, —CH=N—, —S—, or —O—; D represents —(B—O)$_m$—(CO)$_n$—R$^6$ or —B—E, wherein B is lower alkylene, E represents —OSO$_3$H, —SO$_3$H or —COOR$^7$; $R^7$ represents a hydrogen atom or a lower alkyl group and one of $m$ and $n$ is 1 and the other is 0, or $m$ and $n$ each is 1, with the proviso that when D is —B—E and E represents —COOR$^7$, A represents —CH=CH—.

The compounds of this invention show excellent vascular dilator activity and low toxicity and thus are expected to be used safely for diseases of the blood circulatory systems.

DETAILED DESCRIPTION OF THE INVENTION

The compounds of this invention are prepared by reacting the 1,4-dihydropyridine derivative prepared by the method of Hantzsch Pyridine Synthesis and represented by the general formula (II)

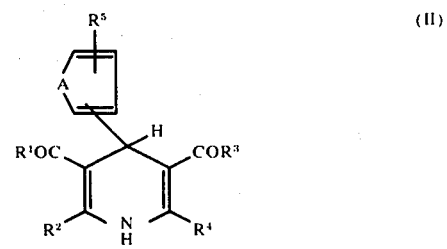

wherein $R^1$, $R^2$, $R^3$, $R^4$, $R^5$, and A have the same significance as in the general formula (I), and an equimolar or preferably excessive molar amount of the halogen compound represented by the general formula (III) or the following formula (III')

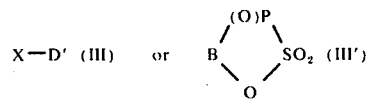

wherein X represents a halogen atom, P represents 0 or 1 and D' represents —(B—O)$_m$—(CO)$_n$—R$^6$ or —B—COOR$^8$ wherein $R^8$ represents a lower alkyl group, in an organic solvent such as tetrahydrofuran, dimethylformamide, dimethylsulfoxide, hexamethylphosphorotriamide, pyridine, etc.

The reaction is ordinarily conducted under anhydrous conditions in the presence of an alkali metal such as metallic sodium, an alkali metal hydride such as sodium hydride, or an alkali metal amide such as sodium amide.

The reaction temperature for the above reaction may be desirably selected from a range of from −50° C. to 120° C.

The compounds of this invention can be prepared by subjecting the aldehyde compound, the acylaceto compound, and the amine each represented by the formulae (IV), (V), and (III′)

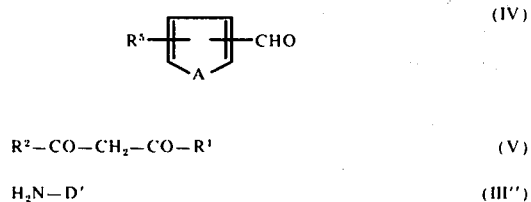

$$R^2-CO-CH_2-CO-R^1 \quad (V)$$

$$H_2N-D' \quad (III'')$$

In the above formulae $R^1$, $R^2$, $R^5$, A, and D′ have the same significance as in the general formula (I) and (III) to the Hantzsch Pyridine Synthesis by the conventional method.

Those methods as mentioned above may be properly selected according to the properties of the desired product and the reactants.

The compounds of this invention prepared by the aforesaid methods may be isolated by a ordinary chemical operation such as extraction, column chromatography, recrystallization, etc.

In the general formula (I) showing the compounds of this invention, examples of the lower alkyl groups having 1 to 7 carbon atoms as represented by the substituents $R^1$, $R^2$, $R^3$, $R^4$, $R^5$, $R^6$, $R^7$ and $R^8$ are a methyl group, an ethyl group, a propyl group, an isopropyl group, an isobutyl group, an n-butyl group, a t-butyl group, a pentyl group, etc., and the lower alkoxy groups also have 1 to 7 carbon atoms, for example a methoxy group, an ethoxy group, an isopropoxy group, a t-butoxy group, an amyloxy group, etc. Also, examples of the lower alkylene group formed by the combination of the substituents $R^1$ and $R^2$ or $R^3$ and $R^4$ having 2 to 7 carbon atoms include an ethylene group, a trimethylene group, a tetramethylene group, etc. Furthermore, examples of the lower alkoxy-substituted alkoxy groups represented by the substituents $R^1$ and $R^2$ are a 2-methoxyethoxy group, a 2-ethoxyethoxy group, a 1-ethoxyethoxy group, etc.

Examples of the lower alkylsulfonyl group represented by the substituent $R^5$ include a methylsufonyl group, an ethylsulfonyl group, an isopropylsulfonyl group, etc.; examples of the di- or mono-lower alkylamino group include a methylamino group, a dimethylamino group, a diethylamino group, an isopropylamino group, a pentylamino group, etc.; and examples of the halogen atom include a chlorine atom, a bromine atom, a fluorine atom, etc.

Examples of the lower alkenyl group represented by the substituent $R^6$ are a vinyl group, a propenyl group, an allyl group, an isopropenyl group, a 1-butenyl group, a 2-butenyl group, etc.

Examples of the lower alkylene group represented by the substituent B include a methylene group, an ethylene group, an ethylidene group, a propylene group, trimethylene group, etc.

Now, the typical examples of the 1-substituted-1,4-dihydropyridine derivatives of this invention are illustrated below although the invention is not limited to them only:

Diethyl 2,6-dimethyl-4-(3-nitrophenyl)-1-isopropoxymethyl-1,4-dihydropyridine-3,5-dicarboxylate,
Diethyl 1-ethoxymethyl-2,6-dimethyl-4-(3-nitrophenyl)-1,4-dihydropyridine-3,5-dicarboxylate,
Diethyl 1-propionyloxymethyl-2,6-dimethyl-4-(3-nitrophenyl)-1,4-dihydropyridine-3,5-dicarboxylate,
Diethyl 2,6-dimethyl-4-(3-nitrophenyl)-1-pivaloyloxymethyl-1,4-dihydropyridine-3,5-dicarboxylate,
Dimethyl 1-ethoxymethyl-4-(2-nitrophenyl)-2,6-dimethyl-1,4-dihydropyridine-3,5-dicarboxylate,
Diethyl 1-(1-ethoxyethyl)-2,6-dimethyl-4-(3-nitrophenyl)-1,4-dihydropyridine-3,5-dicarboxylate,
Bis(2-ethoxyethyl) 1-ethoxymethyl-2,6-dimethyl-4-(3-nitrophenyl)-1,4-dihydropyridine-3,5-dicarboxylate,
Diethyl 4-(3-azidophenyl)-1-ethoxymethyl-2,6-dimethyl-1,4-dihydropyridine-3,5-dicarboxylate,
Dimethyl 4-(4-cyanophenyl)-1-ethoxymethyl-2,6-dimethyl-1,4-dihydropyridine-3,5-dicarboxylate,
Diisopropyl 4-(3-methylsulfonylphenyl)-1-ethoxymethyl-2,6-dimethyl-1,4-dihydropyridine-3,5-dicarboxylate,
Dimethyl 4-(4-dimethylaminophenyl)-1-methoxymethyl-2,6-dimethyl-1,4-dihydropyridine-3,5-dicarboxylate,
Dimethyl 4-(2-chlorophenyl)-1-methoxymethyl-2,6-dimethyl-1,4-dihydropyridine-3,5-dicarboxylate,
Dimethyl 4-(2-furyl)-1-methoxymethyl-2,6-dimethyl-1,4-dihydropyridine-3,5-dicarboxylate,
Dimethyl 4-(2-pyridyl)-1-isopropoxymethyl-2,6-dimethyl-1,4-dihydropyridine-3,5-dicarboxylate,
Dimethyl 4-(5-nitro-2-thienyl)-1-ethoxymethyl-2,6-dimethyl-1,4-dihydropyridine-3,5-dicarboxylate,
Diethyl 4-(4-methylsulfonylphenyl)-1-benzyloxymethyl-2,6-dimethyl-1,4-dihydropyridine-3,5-dicarboxylate,
Diethyl 4-(3-nitrophenyl)-1-ethoxyethyl-2-methyl-6-propyl-1,4-dihydropyridine-3,5-dicarboxylate,
Ethyl 1-ethoxymethyl-2-methyl-4-(3-nitrophenyl)-5-oxo-1,4,5,-6,7,8-hexahydroquinoline-3-carboxylate,
10-Ethoxymethyl-9-(3-nitrophenyl)-1,8-dioxo-1,2,3,4,5,6,7,8,-9,10-decahydroacridine,
Diethyl 1-allyloxymethyl-2,6-dimethyl-4-(3-nitrophenyl)-1,4-dihydropyridine-3,5-dicarboxylate,
Diethyl 2,6-dimethyl-4-(3-nitrophenyl)-1-naphthoyl-1,4-dihydropyridine-3,5-dicarboxylate,
Diethyl 2,6-dimethyl-4-(3-nitrophenyl)-1-p-methylbenzoyl-1,4-dihydropyridine-3,5-dicarboxylate,
Diethyl 2,6-dimethyl-4-(3-nitrophenyl)-1-pyridine-β-carbonyl-1,4-dihydropyridine-3,5-dicarboxylate, and
Sodium β-[2,6-dimethyl-3,5-bis(ethoxycarbonyl)-4-(3-nitrophenyl)-1,4-dihydropyridine-1-yl]ethylsulfate.

A suitable embodiment of the compounds of this invention may be further defined by the following structural formula:

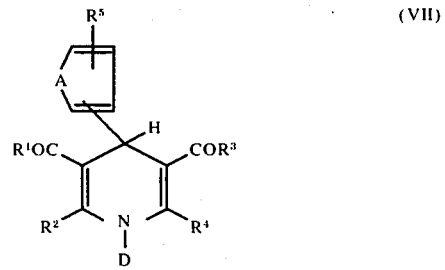

wherein $R^1$ and $R^3$, which may be the same or different, each represent lower alkyl or lower alkoxy which may be substituted by a lower alkoxy group; $R^2$ and $R^4$, which may be the same or different, each represents lower alkyl; $R^5$ represents nitro, halogen, azide, di-lower alkylamino, lower alkoxy or lower alkylsulfonyl when A is —CH=CH—, $R^5$ represents a nitro group when A is sulfur, $R^5$ represents hydrogen when A is —CH=N—, or oxygen; D represents —(B—O)$_m$—(-CO)—$R^6$ or —B—E; B represents lower alkylene; E represents —OSO$_3$H, —SO$_3$H or —COOR$^7$; $R^7$ represents hydrogen or a lower alkyl; and one of $m$ and $n$ is 1 while the other is 0, or $m$ and $n$ are each 1.

A more suitable embodiment of the compounds of this invention are those compounds VII above in which D is —($\beta$—O)$_m$—(CO)$_n$—$R^6$ and $m = 1$, and $n = 1$ and $R^6$ is lower alkyl, lower alkenyl, phenyl or benzyl.

Another more suitable embodiment of the compounds of this invention are those compounds VII above in which D is —B—E; B is lower alkylene and E is —OSO$_3$H or the pharmaceutically acceptable salts thereof.

The novel 1-substituted-1,4-dihydropyridine derivatives of this invention have excellent effects as compared with the aforesaid 1,4-dihydropyridine derivatives known and disclosed in the above-mentioned German patent applications. This will be illustrated by the following experiments.

Experiment 1: Effect on cerebral circulation

Using dogs anesthetized by chloralose-urethane, the carotid blood flow and the vertebral blood flow were measured by means of an electromagnetic flow meter (MF-5 made by Nihon Kohoden Kogyo Co., Ltd.), the regional cerebral blood flow was measured by means of a thermocouple blood flow meter (Shincorder CTE-202 made by K. Shin-Ei Denki Seisaku-sho) according to a heat clearance method, and further the blood pressure was measured by means of a blood pressure transducer (MPU-0.5 made by Nihon Kohoden Kogyo Co., Ltd.).

The results are shown in the following table.

Table 1

| Sample | Dose (mg/Kg) i.v. | Regional Cerebral blood flow Increase ($\mu$V) | Regional Cerebral blood flow Duration (min) | Carotid blood flow Increase (%) | Carotid blood flow Duration (min) | Vertebral blood flow Increase (%) | Vertebral blood flow Duration (min) | Mean blood pressure Decrease (%) |
|---|---|---|---|---|---|---|---|---|
| A | 0.1 | 8.6 | 120 | 80 | 120 | 120 | 100 | 9 |
| B | 0.01 | 9.2 | 30 | 83 | 30 | 130 | 30 | 29 |
| C | 0.01 | 8.2 | 30 | 90 | 30 | 120 | 30 | 28 |
| Papaverine | 1.0 | 8.2 | 7 | 120 | 6 | 120 | 6 | 18 |

A: Diethyl 1-ethoxymethyl-2,6-dimethyl-4-(3'-nitrophenyl)-1,4-dihydropyridine-3,5-dicarboxylate (The compound of the example 2 of the present invention)
B: Diethyl 2,6-dimethyl-4-(3'-nitrophenyl)-1,4-dihydropyridine-3,5-dicarboxylate (Known compound)
C: Dimethyl 2,6-dimethyl-4-(2'-nitrophenyl)-1,4-dihydropyridine-3,5-dicarboxylate (Known compound, Nifedipine, BAY a 1040)

Experiment 2: Acute toxicity in mice

The toxicity of the compounds as used in Experiment 1 was detected and the results as shown in the following table 2 were obtained.

Table 2

| Sample | Dose (mg./kg.) i.p. | Dose (mg./kg.) p.o. |
|---|---|---|
| A | MLD > 3000 | MLD > 5000 |
| B | LD$_{50}$ = 525 | LD$_{50}$ = 5000 |
| C | LD$_{50}$ = 400 | LD$_{50}$ = 2000 |

MLD = Minimum lethal dose.

From the results of the above two experiments it will be understood that the compounds of this invention exerted less influence on the blood pressure and showed such superior effects as increasing the cerebral blood flow remarkably and durably for a long period of time as compared with the known compounds. Furthermore, it is clear that the compounds of this invention showed very low toxicity as compared with the known compound. Thus, the compounds of this invention are more preferable than the known compounds in the point of safety use.

Moreover, the compounds of this invention can increase more effectively the coronary blood flow for a longer period of time as compared with the known compounds and thus are particularly suitable for the treatment of chronic diseases.

Experiment 3

Effects on mean blood pressure (hereinafter referred to as MBP), vertebral blood flow (hereinafter referred to as VBF) and coronary blood flow (hereinafter referred to as Cor.BF), when administered intravenously:

By using dogs anesthetized with pentobarbital, VBF and Cor. BF were measured with an electromagnetic flowmeter. Blood pressure at the femoral artery was measured. The results are shown in the following table.

Table 3

| Sample | Dose mg/kg i.v. | Mean Blood Pressure Decrease ($\Delta$mmHg) | Vertebral Blood Flow Increase ($\Delta$%) | Coronary Blood Flow Increase ($\Delta$%) | Duration (min.) |
|---|---|---|---|---|---|
| D | 0.1 | −5 | 21 | 67 | 20 |
|   | 0.3 | −12 | 75 | 72 | 60 |
|   | 1 | −35 | 169 | 137 | 120 |
| B | 0.001 | −15 | 20 | 58 | 5 |
|   | 0.01 | −35 | 144 | 141 | 30 |
| C | 0.001 | −10 | 47 | 39 | 5 |
|   | 0.01 | −39 | 135 | 144 | 30 |
| E | 0.001 | −16 | 74 | — | 10 |
|   | 0.01 | −44 | 144 | — | 45 |

D: Sodium $\beta$-[2,6-dimethyl-3,5-bis(ethoxycarbonyl)-4-(3-nitrophenyl)-1,4-dihydropyridin-1-yl]-ethylsulfate. (The compound of example 41 of the present invention)
E: 3,5-Dicarboethoxy-1,4-dihydro-2,6-dimethyl-4-(2-trifluoromethylphenyl)pyridine (Known Compound U.S. Patent No. 3,511,847)

From the results of the above Table 3, it will be understood that the compound of this invention (compound D), when administered intravenously, showed such excellent effects as increasing the cerebral blood flow and coronary blood flow and at the same time showed hypotensive activity. It should be noted that these activities were prolonged for a long period of time when compared with known compounds.

Experiment 4

Antagonism against hypertensive action of norepinephrine and effects and MBP and partial oxygen pressure (referred to hereinafter as PO$_2$) in coronary venous blood, in case of intra-duodenal administration:

By using dogs anesthetized by pentobarbital, blood pressure at the femoral artery was measured. For measuring PO$_2$ in coronary venous blood, a cetheter was positioned at the coronary sinus and coronary venous blood was collected and PO$_2$ of the blood was measured with IL meter (Model 113). The results are shown in the following table 4. Antagonism against hypertensive active in case of norepinephrine administration (3g/kg i.v.) was investigated also. Drugs were administered intra-duodenally. (Such administration has the same effect as that of oral administration.) The results are shown in the following table 5.

Table 4

| Sample | Dose mg/ kg i.d. | Item of measurement | Pre-administration | Post-administration (hour) | | | | | |
|---|---|---|---|---|---|---|---|---|---|
| | | | | ½ | 1 | 2 | 3 | 5 | 8 |
| D | 10 | PO$_2$ | 17.8 | 34.7 | 37.2 | 39.7 | 43.3 | 43.2 | 40.0 |
| | | MBP | 110 | −11 | −21 | −32 | −43 | −4.3 | −40 |
| B | 1 | PO$_2$ | 17.4 | 34.6 | 37.7 | 39.3 | 38.9 | 32.7 | 25.0 |
| | | MBP | 101 | −39 | −43 | −42 | −32 | −27 | −12 |
| C | 1 | PO$_2$ | 17.2 | 37.8 | 38.4 | 35.1 | 35.8 | 29.7 | 23.0 |
| | | MBP | 99 | −25 | −28 | −12 | −6 | 0 | −8 |

Table 5

| Sample | Dose mg/kg i.d. | Post-administration (hour) Percent inhibition against increase of blood pressure caused by norepinephrin | | | | | |
|---|---|---|---|---|---|---|---|
| | | ½ | 1 | 2 | 3 | 5 | 8 |
| D | 10 | 69 | 84 | 89 | 89 | 85 | 79 |
| B | 1 | 79 | 78 | 79 | 77 | 63 | 48 |

As shown in the results of the above Tables 4 and 5, effective doses of compounds B and C are 0.01 mg/kg in case of intravenous administration and 1 mg/kg in case of peroral (intra-duodenal) administration. The ratio of these values is 100. On the other hand, the ratio of such values of compound D of the present invention (that is, the ratio of the value in case of intravenous administration to the value in case of peroral administration) is 10. That is, it is understood that compound D is more easily absorbed than compounds B or C, in case of peroral administration. Further, duration time of compound D is much longer than those of compounds B or C. Thus, the compounds of this invention are very useful for the extended treatment (peroral administration) or hypertensive diseases, because compound D shows high absorbability by the digestive tract and shows increasing activity of cerebral and coronary blood flows as well as prolonger hypotensive activity. Further, compound D has excellent water-solubility. That is, the water-solubility of this compound is about 40%, while the water-solubility of compound C is 0.001% and compound B is almost unsoluble in water.

The compounds of this invention may be administered orally or parenterally in conventional dosage unit forms such as tablets, capsules, injections, and the like by incorporating the appropriate doses of 10–100 mg. orally or 1–10 mg. intravenously for a man in a day, which is changeble upon the condition and age of the patient.

Now, the invention will further be explained more practically by the following examples.

EXAMPLE 1

In 10 ml of anhydrous tetrahydrofuran was suspended 482 mg of a 50% oil dispersion of sodium hydride and after adding to the mixture 15 ml. of anhydrous tetrahydrofuran solution of 2.5 g of diethyl 2,6-dimethyl-4-(3-nitrophenyl)-1,4-dihydropyridine-3,5-dicarboxylate, the resultant mixture was stirred at room temperature for a while. The mixture was cooled to temperatures of from −40° C. to −50° C. and after adding dropwise to the mixture 10 ml. of anhydrous tetrahydrofuran solution of 1.57 g. of isopropoxymethyl chloride at the same temperature as above, the mixture was stirred for 5 minutes at room temperature. The reaction product was mixed with 50 ml. of water and then extracted twice with ethyl acetate. The ethyl acetate extract was washed with water, dried over anhydrous magnesium sulfate, and the solvent was removed under a reduced pressure. The residue formed was subjected to a silica gel column chromatography, developed with a 1:4 mixed solvent of hexane and benzene and then eluted with a 40:1 mixed solvent of benzene and ethyl acetate. The effluent was examined by a thin layer chromatography and the main fraction effluent recovered was concentrated to provide 2.3 g of white crystals of diethyl 2,6-dimethyl-4-(3-nitrophenyl)-1-isopropoxymethyl-1,4-dihydropyridine-3,5-dicarboxylate melting at 117° C. The product was confirmed in the infrared absorption spectra and the nuclear magnetic resonanace spectra to completely coincide with the presumed structure.

| Elemental analysis for $C_{23}H_{30}N_2O_7$: | | |
|---|---|---|
| | C(%) | H(%) | N(%) |
| Calculated: | 61.87 | 6.77 | 6.27 |
| Found: | 61.72 | 6.93 | 6.21 |

EXAMPLE 2

In 5 ml. of anhydrous tetrahydrofuran was suspended 193 mg. of a 50% oil dispersion of sodium hydride and after adding to the mixture 7 ml of anhydrous tetrahydrofuran solution of 1 g. of diethyl 2,6-dimethyl-4-(3-nitrophenyl)-1,4-dihydropyridine-3,5-dicarboxylate, the resultant mixture was stirred at room temperature for a while. The red-brown reaction product thus obtained was cooled to temperatures of from −40° C. to −50° C. and after adding thereto 5 ml. of anhydrous tetrahydrofuran solution of 380 mg. of ethoxymethyl chloride at the same temperature, the mixture was stirred for one hour and 45 minutes at the same temperature. By treating further the reaction product as in Example 1,370 mg. of white crystals of diethyl 1-ethoxymethyl-2,6-dimethyl-4-(3-nitrophenyl)-1,4-dihydropyridine-3,5-dicarboxylate melting at 125° C. was obtained. The product was confirmed in the infrared absorption spectra and the nuclear magnetic resonance spectra to completely coincide with the presumed structure.

| Elemental analysis for $C_{22}H_{28}N_2O_7$: | | |
|---|---|---|
| | C(%) | H(%) | N(%) |
| Calculated: | 61.10 | 6.53 | 6.48 |
| Found: | 61.03 | 6.71 | 6.31 |

EXAMPLE 3

A mixture of 10 g. of diethyl 2,6-dimethyl-4-3-nitrophenyl)-1,4-dihydropyridine-3,5-dicarboxylate, 2.0 g. of 50% oil dispersion of sodium hydride, and 110 ml. of anhydrous tetrahydrofuran was stirred for 30 minutes at room temperature. The reaction product thus obtained was cooled to −40° C. and after adding to the product 10 ml. of propionyloxymethyl chloride at the same temperature as above, the resultant mixture was allowed to stand at −40° C. for a while. Then, 2 ml. of glacial acetic acid, ether, and water were added to the mixture and the ether layer formed was recovered. After washing the ether layer with water and drying it over anhydrous magnesium sulfate, ether was removed under a reduced pressure. The crystalline precipitate was filtered off and the crystals were washed with a small amount of ether. The ether used for washing was combined with the filtrate and ether was removed therefrom. The residue was subjected to a silica gel column chromatography, using a 20:1 benzene-ethyl acetate mixed solvent as an eluant and the effluent was concentrated to provide faint yellow crystals of diethyl 1-propionyloxymethyl-1,6-dimethyl-4-(3-nitrophenyl)-1,4-dihydropyridine-3,5-dicarboxylate. After recrystallizing from benzene-hexane, the product melted at 102°–104° C. The amount of the product obtained was 2 g.

The product was confirmed in the infrared absorption spectra and the nuclear magnetic resonance spectra to completely coincide with the presumed structure.

| Elemental analysis as $C_{23}H_{28}N_2O_8$: | | | |
|---|---|---|---|
| | C(%) | H(%) | N(%) |
| Calculated: | 59.99 | 6.13 | 6.08 |
| Found: | 60.12 | 6.13 | 6.05 |

EXAMPLE 4

A mixture of 10 g. of diethyl 2,6-dimethyl-4-(3-nitrophenyl)-1,4-dihydropyridine-3,5-dicarboxylate, 2.0 g of a 50% oil dispersion of sodium hydride, and 110 ml. of anhydrous tetrahydrofuran was stirred for 30 minutes at room temperature. The reaction product was cooled to −40° C. and after adding thereto 10 ml. of pivaloyloxymethyl chloride at the same temperature, the resultant mixture was allowed to stand for 4 hours at room temperature. By treating the product as in Example 3, faint yellow crystals of diethyl 2,6-dimethyl-4-(3-nitrophenyl)-1-pivaloyloxymethyl-1,4-dihydropyridine-3,5-dicarboxylate was obtained. After recrystallizing from benzene-hexane the product melted at 133°–134° C., yield 1.1 g.

Then product was confirmed in the infrared absorption spectra and the nuclear magnetic resonance spectra to completely coincide with the presumed structure.

| Elemental analysis for $C_{25}H_{32}N_2O_8$: | | | |
|---|---|---|---|
| | C(%) | H(%) | N(%) |
| Calculated: | 61.46 | 6.60 | 5.73 |
| Found: | 61.65 | 6.53 | 5.62 |

By following the same procedure as above except that 10 ml. of pivaloyloxymethyl bromide or 10 ml. of pivaloyloxymethyl iodide was used in place of 10 ml. of pivaloyloxymethyl chloride, diethyl 2,6-dimethyl-4-(5-nitrophenyl)-1-pivaloyloxymethyl-1,4-dihydropyridine-3,5-dicarboxylate was obtained.

EXAMPLE 5

In 75 ml. of anhydrous tetrahydrofuran was dissolved 5 g. of dimethyl 2,6-dimethyl-4-(3-nitrophenyl)-1,4-dihydropyridine-3,5-dicarboxylate in a nitrogen gas stream and after adding to the solution 1.25 g. of 50% oil dispersion of sodium hydride, the resultant mixture was stirred for 10 minutes at room temperature. Then, the mixture was cooled to −40° C., and after adding thereto 3 ml. of ethoxymethyl chloride at the same temperature and stopping the cooling, the mixture was stirred for 30 minutes. After the reaction was over, 1 ml. of glacial acetic acid was added to the reaction product and then the mixture was diluted with ethyl acetate. The reaction product was, then, washed with water, saturated aqueous sodium bicarbonate, and then water, dried over anhydrous magnesium sulfate, and the solvent was distilled away under a reduced pressure to provide crude dimethyl N-ethoxymethyl-2,6-dimethyl-4-(3-nitrophenyl)-1,4-dihydropyridine-3,5-dicarboxylate. By recrystallizing the product from benzene-n-hexane, 5.05 g. of white acicular crystals melting at 85° – 86° C. were obtained.

The product was confirmed in the infrared absorption spectra, the nuclear magnetic resonance spectra, and the mass analysis spectra to completely coincide with the presumed structure.

| Elemental analysis for $C_{20}H_{24}N_2O_7$: | | | |
|---|---|---|---|
| | C(%) | H(%) | N(%) |
| Calculated: | 59.40 | 5.98 | 6.93 |
| Found: | 59.62 | 5.87 | 6.98 |

EXAMPLE 6

In 7 ml. of anhydrous tetrahydrofuran was dissolved 5 g. of dimethyl 2,6-dimethyl-4-(2-nitrophenyl)-1,4-dihydropyridine-3,5-dicarboxylate in a nitrogen gas stream and after adding to the solution 1.25 g. of a 50% oil dispersion of sodium hydride, the mixture was stirred for 10 minutes at room temperature. Then, 3 ml. of ethoxymethyl chloride was added to the mixture under cooling to −'° C. and after removing the cooling bath, the mixture was stirred for 30 minutes. By treating the product as in Example 5, a crude product was obtained and further by recrystallizing the product from benzene-n-hexane, 3.7 g of white acicular crystals of dimethyl N-ethoxymethyl-4-(2-nitrophenyl)-2,6-dimethyl-1,4-dihydropyridine-3,5-dicarboxylate melting at 130° – 131° C. were obtained.

The product was confirmed in the infrared absorption spectra, the nuclear magnetic resonance spectra, and the mass analysis spectra to completely coincide with the presumed structure.

| Elemental analysis for $C_{20}H_{24}N_2O_7$: | | | |
|---|---|---|---|
| | C(%) | H(%) | N(%) |
| Calculated: | 59.40 | 5.98 | 6.93 |
| Found: | 59.56 | 5.93 | 6.86 |

In addition, the mother liquor obtained in the crystallization was subjected to a silica gel column chromatography followed by treating with a 20:1 benzene-ethyl acetate mixed solvent and from the fraction of the first yellow band, 0.6 g. of dimethyl N-ethoxymethyl-4-(2- nitrophenyl)2,6-dimethyl-1,4-dihydropyridine-3,5-dicarboxylate melting at 130°–131° C. was recovered. When the product was mixed with the crystals obtained by the recrystallization in the above procedure, no depression of melting point was shown.

Also, from the fraction of the second yellow band, 1.5 g. of dimethyl N,3-bis(ethoxymethyl)-4-(2-nitrophenyl)-6-methyl-2-methylene-1,2,3,4-tetrahydropyridine-3,5-dicarboxylate was obtained as a faint yellow oily material.

The product was confirmed in the infrared absorption spectra, the nuclear magnetic resonance spectra, and the mass analysis spectra to completely coincide with the presumed structure.

| Elemental analysis for $C_{23}H_{30}N_2O_8$: | | |
|---|---|---|
| C(%) | H(%) | N(%) |
| Calculated: 59.37 | 6.54 | 6.06 |
| Found: 59.63 | 6.57 | 6.02 |

EXAMPLE 7

In 50 ml. of anhydrous tetrahydrofuran was dissolved 5 g. of diethyl 2,6-dimethyl-4-(3-nitrophenyl)-1,4-dihydropyridine 3,5-dicarboxylate in a nitrogen gas stream and after adding to the solution 1 g. of a 50% oil dispersion of sodium hydride, the mixture was maintained at room temperature for 10 minutes. Then, 3 ml. of 1-chloro-1-ethoxyethane was added to the mixture under cooling to −40° C. and after removing the cooling bath, the resultant mixture was stirred for 30 minutes. After the reaction was over, 1 ml. of glacial acetic acid was added to the product and then the product was diluted with ethyl acetate. The reaction product was washed with water, saturated aqueous sodium bicarbonate solution, and then water, dried over anhydrous magnesium sulfate, and then the solvent was distilled away under a reduced pressure to provide crude diethyl N-(1-ethoxyethyl)-2,6-dimethyl-4-(3-nitrophenyl)-1,4-dihydropyridine-3,5-dicarboxylate. By purifying the product by means of a silica gel column chromatography and by using a 20:1 benzeneethyl acetate mixed solvent, 1 g. of faint-yellow oily diethyl N-(1-ethoxyethyl)-2,6-dimethyl-4-(3-nitrophenyl)-1,4-dihydropyridine-3,5-dicarboxylate was obtained. The product was confirmed in the infrared absorption spectra, the nuclear magnetic resonance spectra, and the mass analysis spectra to completely coincide with the presumed structure.

| Elemental analysis for $C_{23}H_{30}N_2O_7$: | | |
|---|---|---|
| C(%) | H(%) | N(%) |
| Calculated: 61.87 | 6.77 | 6.27 |
| Found: 62.13 | 6.75 | 6.03 |

EXAMPLE 8

In 20 ml. of anhydrous tetrahydrofuran was dissolved 10 g. of bis(2-ethoxyethyl) 2,6-dimethyl-4-(3-nitrophenyl)-1,4-dihydropyridine-3,5-dicarboxylate and then the solution was added dropwise to 10 ml. of an anhydrous tetrahydrofuran suspension of 1.2 g. of a 50% oil dispersion of sodium hydride under stirring. After stirring the mixture further for 30 minutes at room temperature, the mixture was cooled to −10° C., 5 ml. of anhydrous tetrahydrofuran solution of 2.5 g. of chloromethoxyethane was added thereto over a period of 15 minutes, the temperature of the system was elevated gradually up to 0° C. over a period of about 15 minutes, and then the mixture was maintained at 0° C. for 15 minutes. The reaction product was cooled again to −10° C. and 2 ml. of acetic acid was added to the product. After stopping the cooling, 100 ml. of water was added to the product and then the product was extracted three times each time with 30 ml. of ether. The ether extracts were combined, dried over anhydrous sodium sulfate and then ether was distilled away. By recrystallizing the residue from 20:1 hexane-ethanol mixed solvent, 8.6 g. of colorless plate crystals of bis(2-ethoxyethyl) N-ethoxymethyl-2,6-dimethyl-4-(3-nitrophenyl)-1,4-dihydropyridine-3,5-dicarboxylate melting at 63°–63.5° C. were obtained.

The product was confirmed in the infrared absorption spectra, the nuclear magnetic resonance spectra, and the mass analysis spectra to completely coincide with the presumed structure.

| Elemental analysis for $C_{26}H_{36}N_2O_9$: | | |
|---|---|---|
| C(%) | H(%) | N(%) |
| Calculated: 59.98 | 6.97 | 5.38 |
| Found: 60.02 | 6.95 | 5.34 |

EXAMPLE 9

In 10 ml. of anhydrous tetrahydrofuran was dissolved 3.7 g. of diethyl 4-(3-azidophenyl)-2,6-dimethyl-1,4-dihydropyridine-3,5-dicarboxylate and the solution was added dropwise to 5 ml of the anhydrous tetrahydrofuran dispersion of 0.7 g. of a 50% oil dispersion of sodium hydride with stirring. After stirring the mixture for 30 minutes at room temperature, the mixture was cooled to −10° C. and then 5 ml. of anhydrous tetrahydrofuran solution of 1.9 g. of chloromethoxyethane was added to the mixture over a period of 15 minutes at the temperature. The reaction product was then treated as in Example 8 and the residue thus otained was recrystallized from a 20:1 n-hexane-ethanol mixed solvent to provide 2.5 g. of the colorless acicular crystal of diethyl 4-(3-azidophenyl)-N-ethoxymethyl-2,6-dimethyl-1,4-dihydropyridine-3,5-dicarboxylate melting at 102°–103° C.

The product was confirmed in the infrared absorption spectra, the nuclear magnetic resonance spectra, and the mass analysis spectra to completely coincide with the presumed structure.

| Elemental analysis for $C_{22}H_{28}N_4O_5$: | | |
|---|---|---|
| C(%) | H(%) | N(%) |
| Calculated: 61.67 | 6.59 | 13.08 |
| Found: 61.46 | 6.60 | 13.12 |

EXAMPLES 10–24

By following the procedures explained in the aforesaid examples the novel compounds of this invention shown in the following table were prepared. In the table, $R^1$, $R^2$, $R^3$, $R^4$, B, A, and n of the starting material (I) and the reactant (II) were same as those of the desired products (III) corresponding to them.

Table

| Ex. No. | Amount of starting material (I) (g) | Reactant (II) X | Amount (ml) | Aimed Product (III) R¹ | R² | R³ | R⁴ | R⁶ | B | A with R⁵ | n | m |
|---|---|---|---|---|---|---|---|---|---|---|---|---|
| 10 | 1 | Cl | 0.6 | —O—CH₃ | —CH₃ | —O—CH₃ | —CH₃ | —CH₂CH₃ | —CH₂— | 4-NO₂-phenyl | 0 | 1 |
| 11 | 1 | Cl | 0.6 | —O—CH₃ | —CH₃ | —O—CH₃ | —CH₃ | —CH₂CH₃ | —CH₂— | 4-CN-phenyl | 0 | 1 |
| 12 | 1 | Cl | 0.5 | —O—CH₃ | —CH₃ | —O—CH₃ | —CH₃ | —CH₂CH₃ | —CH₂— | 2-SO₂CH₃-phenyl | 0 | 1 |
| 13 | 1 | Cl | 0.46 | —O—CH(CH₃)₂ | —CH₃ | —O—CH(CH₃)₂ | —CH₃ | —CH₂CH₃ | —CH₂— | 3-SO₂CH₃-phenyl | 0 | 1 |
| 14 | 1 | Cl | 0.4 | —O—CH₂CH₃ | —CH₃ | —O—CH₂CH₃ | —CH₃ | —CH₃ | —CH₂— | 3-SO₂CH₃-phenyl | 0 | 1 |
| 15 | 1 | Cl | 0.41 | —O—CH₃ | —CH₃ | —O—CH₃ | —CH₃ | —CH₃ | —CH₂— | 4-N(CH₃)₂-phenyl | 0 | 1 |
| 16 | 1 | Cl | 0.41 | —O—CH₃ | —CH₃ | —O—CH₃ | —CH₃ | —CH₃ | —CH₂— | 3-OCH₃-phenyl | 0 | 1 |

| | | | | | | |
|---|---|---|---|---|---|---|
| 17 | 1 | Cl | 0.41 | —O—CH₃ | —O—CH₃ | —CH₃ | —CH₃ |  | —CH₂— |  | 0 | 1 |
| 18 | 1 | Cl | 0.45 | —O—CH₃ | —O—CH₃ | —CH₃ | —CH₃ | | —CH₂— | | 0 | 1 |
| 19 | 1 | Cl | 0.7 | —O—CH₃ | —O—CH₃ | —CH₃ | —CH(CH₃)₂ | | —CH₂— | | 0 | 1 |
| 20 | 1 | Cl | 0.7 | —O—CH₃ | —O—CH₃ | —CH₃ | —CH(CH₃)₂ | | —CH₂— | | 0 | 1 |
| 21 | 0.25 | Cl | 0.14 | —O—CH₃ | —O—CH₃ | —CH₃ | —CH₂CH₃ | | —CH₂— | | 0 | 1 |
| 22 | 1 | Cl | 0.84 | —O—CH₂CH₃ | —O—CH₂CH₃ | —CH₃ | —CH₃ |  | —CH₂— | | 0 | 1 |
| 23 | 0.5 | Cl | 0.42 | —O—CH₃ | —O—CH₃ | —CH₃ | —CH₃ | | —CH₂— | | 0 | 1 |
| 24 | 0.5 | Cl | 0.42 | —O—CH₃ | —O—CH₃ | —CH₃ | —CH₃ | | —CH₂— | | 0 | 1 |

Table-continued

| | Yield (g) | m.p. (° C) | Note |
|---|---|---|---|
| 10 | 0.9 | 126–127 | Same procedure as in Example 5 except that a mixture of 5 ml. of tetrahydrofuran and 4 ml. of dimethylformamide was used as the solvent and ethyl acetate-hexane was used as the solvent for recrystallization. |
| 11 | 0.88 | 98 | Same procedure as in Example 5 except that a mixture of 10 ml. of tetrahydrofuran and 4 ml. of dimethylformamide was used as the solvent and ethyl acetate-hexane was used as the solvent for recrystallization. |
| 12 | 0.85 | 134.5–135.5 | Same procedure as in Example 5 except that a mixture of 20 ml. of tetrahydrofuran and 4 ml. of dimethylformamide was used as the solvent. |
| 13 | 0.8 | 74–75 | Same procedure as in Example 5 except that a mixture of 15 ml. of tetrahydrofuran and 4 ml. of dimethylformamide was used as the solvent. |
| 14 | 0.9 | 134–135 | Same procedure as in Example 5 except that a mixture of 10 ml. of tetrahydrofuran and 4 ml. of dimethylformamide was used as the solvent. |
| 15 | 0.8 | 170–171 | Same procedure as in Example 5 except that a mixture of 15 ml. of tetrahydrofuran and 4 ml. of dimethylformamide was used as the solvent and ethyl acetate was used as the solvent for recrystallization. |
| 16 | 0.95 | 111–112 | Same procedure as in Example 5 except that a mixture of 10 ml. of tetrahydrofuran and 4 ml. of dimethylformamide was used as the solvent. |
| 17 | 0.8 | 159–160 | Same procedure as in Example 5 except that a mixture of 10 ml. of tetrahydrofuran and 4 ml. of dimethylformamide was used as the solvent and ethyl acetate was used as the solvent for recrystallization. |
| 18 | 0.8 | 141–142 | '' |
| 19 | 0.7 | 151–152 | Same procedure as in Example 5 except that ethyl acetate was used as the solvent for recrystallization. |
| 20 | 0.5 | 124–125 | Same procedure as in Example 5 except that a mixture of 10 ml. of tetrahydrofuran and 4 ml. of dimethylformamide was used as the solvent and ethyl acetate-hexane was used as the solvent for recrystallization. |
| 21 | 0.27 | 115–116 | Same procedure as in Example 5. |
| 22 | 1.1 | 86–87 | '' |
| 23 | 0.6 | 151–152.5 | '' |
| 24 | 0.6 | 122–124 | '' |

Now, the preparations of some of the starting materials used in the above examples will be further described below.

Preparation of the starting material in Example 23:

A mixture of 2.2 g of p-methylsulfonyl benzaldehyde, 2.8 g. of methyl acetoacetate, and 6 ml. of methanol containing 0.2 g. of ammonia was maintained for 5 hours at 100° C. in a pressure vessel. After cooling, the reaction product was concentrated under a reduced pressure and the residue was recrystallized from methanol to provide 1.8 g. of faint-yellow columnar crystals of dimethyl 2,6-dimethyl-4-(4-methylsulfonylphenyl)-1,4-dihydropyridine-3,5-dicarboxylate melting at 224°–225° C. with a yield of 39%.

| Elemental analysis for | C(%) | H(%) | N(%) | S(%) |
|---|---|---|---|---|
| Calculated: | 57.26 | 5.60 | 3.85 | 8.47 |
| Found: | 56.98 | 5.58 | 3.69 | 8.45 |

Preparation of the starting material in Examples 24 & 14:

By following the above procedure using m-methylsulfonylbenzaldehyde, methyl acetoacetate, and ammonia, faint-yellow columnar crystals of dimethyl 2,6-dimethyl-4-(3-methylsulfonylphenyl)-1,4-dihydropyridine-3,5-dicarboxylate melting at 153°–154° C. was obtained with a yield of 79%.

Furthermore, the corresponding diethyl ester was also obtained as faint-yellow columnar crystals melting at 180° C. with a yield of 60%.

Preparation of the starting material in Example 12:

By following the above procedure as in the case of preparing the starting material in Example 23 using o-methylsulfonyl benzaldehyde and then finally recrystallizing the product from hydrous dimethylformamide, faint-yellow acicular crystals of dimethyl 2,6-dimethyl-4-(2-methylsulfonylphenyl)-1,4-dihydropyridine-3,5-dicarboxylate melting at 279°–282° C. was obtained with a yield of 32%.

| Elemental analysis | N(%) | S(%) |
|---|---|---|
| Calculated: | 3.65 | 8.42 |
| Found: | 3.69 | 8.45 |

Furthermore, the corresponding diethyl ester was obtained as faint-yellow acicular crystals melting at 235°–236° C. with a yield of 39%.

| Elemental analysis | S(%) |
|---|---|
| Calculated: | 7.83 |
| Found: | 7.87 |

Preparation of the starting material in Example 21:

By following the same procedure as in the case of preparing the starting material in Example 23 using 5-nitro-2-thiophene aldehyde, yellow acicular crystals of dimethyl 2,6-dimethyl-4-(5-nitro-2-thienyl)-1,4-dihydropyridine-3,5-dicarboxylate melting at 192° C. were obtained with a yield of 36%.

| Elemental analysis | C(%) | H(%) | N(%) | S(%) |
|---|---|---|---|---|
| Calculated: | 51.00 | 4.56 | 8.01 | 8.97 |
| Found: | 51.13 | 4.58 | 7.95 | 9.10 |

Furthermore, the corresponding diethyl ester was also obtained as yellow acicular crystals (recrystallized from hydrous ethanol) melting at 141°–142° C. with a yield of 25%.

| Elemental analysis | C(%) | H(%) | N(%) | S(%) |
|---|---|---|---|---|
| Calculated: | 53.62 | 5.32 | 7.32 | 8.43 |
| Found: | 53.67 | 5.30 | 7.36 | 8.43 |

EXAMPLE 25

In 7 ml. of tetrahydrofuran was dissolved 0.5 g. of methylethyl 2,6-dimethyl-4-(3-nitrophenyl)-1,4-dihydropyridine-3,5-dicarboxylate and after adding to the solution 0.2 g. of a 50% oil dispersion of sodium hydride, the mixture was stirred for 30 minutes at room temperature. After cooling the mixture to −10° C., 0.5 ml. of chloromethoxyethane was added and the temperature of the mixture was elevated to room temperature again over a period of about 20 minutes. After 15 minutes, the reaction product was cooled again to −10° C. and after adding thereto 0.5 ml. of glacial acetic acid and 20 ml. of water, the product was extracted three times each time with 5 ml. of ether at room temperature. The extracts were combined, washed with 5 ml. of saturated sodium bicarbonate solution, dried over anhydrous sodium sulfate, and ether was distilled away. The residue was subjected to a silica gel chromatography, using a 10 : 1 benzene-acetone mixed solvent as an eluant, the effluent was examined by a thin layer of chromatography, and then the effluent of the main fraction was recovered and concentrated. By recrystallizing the residue thus obtained from a 10 : 1 benzene-hexane mixed solvent, 0.4 g. of colorless acicular crystals of methylethyl 1-ethoxymethyl-2,6-dimethyl-4-(3-nitrophenyl)-1,4-dihydropyridine-3,5-dicarboxylate melting at 92°–94° C. were obtained.

| Elemental analysis for $C_{21}H_{26}N_2O_7$: | C(%) | H(%) | N(%) |
|---|---|---|---|
| Calculated: | 60.28 | 6.26 | 6.70 |
| Found: | 60.25 | 6.28 | 6.66 |

EXAMPLE 26

By following the same procedure as in Example 25 except that 0.5 g. of diethyl 2-methyl-6-propyl-4-(3-nitrophenyl)-1,4-dihydropyridine-3,5-dicarboxylate and 0.5 g. of chloromethoxyethane were used as the starting materials, benzene was used as the eluant, and hexane was used as the solvent for recrystallization, 0.35 g. of colorless acicular crystals of diethyl 1-ethoxymethyl-2-methyl-4-(3-nitrophenyl)-6-propyl-1,4-dihydropyridine-3,5-dicarboxylate melting at 97° C. were obtained.

| Elemental analysis for $C_{24}H_{32}N_2O_7$: | | |
|---|---|---|
| | C(%) | H(%) | N(%) |
| Calculated: | 62.59 | 7.00 | 6.08 |
| Found: | 62.60 | 6.98 | 6.15 |

EXAMPLE 27

In 10 ml. of tetrahydrofuran was dissolved 0.5 g. of diethyl 4-(3-nitrophenyl)-2,6-dipropyl-1,4-dihydropyridine-3,5-dicarboxylate and after adding to the solution 0.2 g. of a 50% oil dispersion of sodium hydride, the mixture was stirred for 2 hours at room temperature. After cooling the mixture to −20° C., 0.5 ml. of chloromethoxyethane was added thereto and the mixture reacted for 1.5 hours at temperatures of from −20° C. to −10° C. After adding to the reaction product 0.5 ml. of glacial acetic acid and 20 ml. of water, the product was extracted three times each time with 5 ml. of ether at room temperature. The extracts were combined, washed with 5 ml. of saturated aqueous sodium bicarbonate solution, dried over anhydrous sodium sulfate, and the ether was distilled away. The residue was subjected to a silica gel column chromatography, using a 10 : 1 benzene-acetone mixed solvent as an eluant, the effluent thus recovered was examined by a thin layer chromatography, and the effluent of the main fraction recovered was concentrated. By recrystallizing the residue formed from hexane, 0.4 g. of colorless acicular crystals of diethyl 1-ethoxymethyl-4-(3-nitrophenyl)-2,6-dipropyl-1,4-dihydropyridine-3,5-dicarboxylate melting at 109°–110° C. were obtained.

| Elemental analysis for $C_{26}H_{36}N_2O_7$: | | |
|---|---|---|
| | C(%) | H(%) | N(%) |
| Calculated: | 63.92 | 7.43 | 5.73 |
| Found: | 63.86 | 7.52 | 5.71 |

EXAMPLE 28

To 100 ml. of dessicated dimethylformamide were added 6 g. of diethyl 2,6-dimethyl-4-(3-nitrophenyl)-1,4-dihydropyridine-3,5-dicarboxylate and 0.75 g. of a 50% oil dispersion of sodium hydride and then the mixture was stirred for 2 hours at room temperature. To the mixture was added 6 ml. of anhydrous dimethylformamide solution of 3.6 g. of anhydride benzoic and the resultant mixture was stirred for 30 minutes at room temperature.

After adding to the reaction product 150 ml. of water, the product was extracted with ether and the ether extract was washed with 10% sodium carbonate solution and then water, and dried over anhydrous sodium sulfate. The solvent was, then, distilled away under a reduced pressure, ether and petroleum ether were added to the residue, and then 4.0 g. of crystals of the unreacted diethyl 2,6-dimethyl-4-(3-nitrophenyl)-1,4-dihydropyridine-3,5-dicarboxylate thus precipitated were filtered off.

The filtrate was concentrated under a reduced pressure and the residue was subjected to a silica gel chromatography. By separating the product using a 40 : 1 benzene-ether mixed solvent as an eluant, 55.2 mg. of crude crystals of diethyl 1-benzoyl-2,6-dimethyl-4-(3-nitrophenyl)-1,4-dihydropyridine-3,5-dicarboxylate were obtained. By recrystallizing the crude crystal from 1 : 6 : 3 acetone-ether-petroleum ether mixed solvent, 310 mg. of diethyl 1-benzoyl-2,6-dimethyl-4-(3-nitrophenyl)-1,4-dihydropyridine-3,5-dicarboxylate in the form of crystls melting at 98°–101° C. were obtained.

| Elemental analysis for $C_{26}H_{26}N_2O_7$: | | |
|---|---|---|
| | C(%) | H(%) | N(%) |
| Calculated: | 65.26 | 5.48 | 5.86 |
| Found: | 65.00 | 5.32 | 5.53 |

EXAMPLE 29

To 20 ml. of anhydrous dimethylformamide were added 2 g. of diethyl 2,6-dimethyl-4-(3-nitrophenyl)-1,4-dihydropyridine-3,5-dicarboxylate and 0.2 g. of a 50% oil dispersion of sodium hydride and the mixture was stirred for 2 hours at room temperature. To the mixture was added 2 ml. of anhydride propionic and then the resultant mixture was stirred for 30 minutes at room temperature. After adding 40 ml. of water to the reaction product, the resulting mixture was extracted with ether and the ether extract as washed with 10% aqueous sodium carbonate solution and then water and dried over anhydrous sodium sulfate. The solvent was distilled away from the product under a reduced pressure, ether and petroleum ether was added to the residue formed, and then 0.759 g. of the crystalline unreacted diethyl 2,6-dimethyl-4-(3-nitrophenyl)-1,4-dihydropyridine-3,5-dicarboxylate was filtered off.

The filtrate was concentrated under a reduced pressure and the residue was subjected to a silica gel column chromatography. By separating the product using a 10 : 1 benzene-ethyl acetate mixed solvent as an eluant, 170 mg. of oily diethyl 2,6-dimethyl-4-(3-nitrophenyl)-1-propionyl-1,4-dihydropyridine-3,5-dicarboxylate was obtained.

| Elemental analysis for $C_{22}H_{26}N_2O_7$: | | |
|---|---|---|
| | C(%) | H(%) | N(%) |
| Calculated: | 61.39 | 6.09 | 6.51 |
| Found: | 61.03 | 5.99 | 6.32 |

EXAMPLE 30

To 20 ml. of anhydrous dimethylformamide were added 2 g. of diethyl 2,6-dimethyl-4-(3-nitrophenyl)-1,4-dihydropyridine-3,5-dicarboxylate and 0.2 g. of a 50% oil dispersion of sodium hydride and the mixture was stirred for 2 hours at room temperature. After cooling the mixture to −5° C., 2 ml. of anhydride propionic was added and the resultant mixture was stirred for 30 minutes at the same temperature. Then, by treating the reaction product as in Example 29, 1.0 g. of the unreacted diethyl 2,6-dimethyl-4-(3-nitrophenyl)-1,4-dihydropyridine-3,5-dicarboxylate in crystalline form was filtered off. The filtrate was concentrated under a reduced pressure and the residue was subjected to a silica gel column chromatography. By separating the product using a 10 : 1 benzene-ethyl acetate mixed solvent as an eluant, there was obtained 325 mg. of diethyl 2,6-dimethyl-4-(3-nitrophenyl)-1-(1-propionyloxy-1-propenyl)-1,4-dihydropyridine-3,5-dicarboxylate in crystalline form melting at 101°–103° C.

Mass analysis spectrum: m/e: 486(M$^+$)

Infrared absorption spectra:

1760 m.⁻¹ carbonyl(enol ester)
1680 m.⁻¹ carbonyl(ethyl ester)

Elemental analysis for $C_{25}H_{30}O_8N_2$:

| | C(%) | H(%) | N(%) |
|---|---|---|---|
| Calculated: | 61.39 | 6.09 | 6.51 |
| Found: | 61.60 | 6.30 | 6.33 |

In addition, the filtrate formed after recovering by filtration the crystals of diethyl 2,6-dimethyl-4-(3-nitrophenyl)-1-(1-propionyloxy-1-propenyl)-1,4-dihydropyridine-3,5-dicarboxylate was concentrated, subjected to a silica gel thin layer chromatography, developed using a 200 : 6 benzene-ethyl acetate mixed solvent, the fractions corresponding to Rf = 0.4 were collected, and extracted with methanol. From the extract 250 mg. of diethyl 2,6-dimethyl-4-(3-niytrophenyl)-1-propionyl-1,4-dihydropyridine-3,5-dicarboxylate was obtained.

EXAMPLE 31

In 10 ml. of dimethylformamide was dissolved 1 g. of diethyl 2,6-dimethyl-4-(3-nitrophenyl)-1,4-dihydropyridine-3,5-dicarboxylate and after adding to the solution 0.1 g. of sodium hydride, the mixture was stirred for 30 minutes at room temperature. To the mixture was added 1 ml. of acetic anhydride and the resultant mixture was stirred for one hour at room temperature. After adding to the reaction product 20 ml. of water, the product was extracted twice each time with ether. The extracts were washed with 10 ml. of water, dried over anhydrous sodium sulfate, and then the solvent was distilled away under a reduced pressure. The residue was subjected to a silica gel column chromatography, and the product was separated using a 10 : 1 benzene-acetone mixed solvent as an eluant to provide 0.5 g. of the yellow viscous liquid of diethyl 1-acetyl-2,6dimethyl-4-(3-nitrophenyl)-1,4-dihydropyridine-3,5-dicarboxylate.

Elemental analysis for $C_{21}H_{24}N_2O_7$:

| | C(%) | H(%) | N(%) |
|---|---|---|---|
| Calculated: | 60.57 | 5.81 | 6.73 |
| Found: | 60.18 | 6.03 | 6.55 |

EXAMPLE 32

In 7 ml. of tetrahydrofuran was dissolved 0.5 g. of ethyl 3-acetyl-2,6-dimethyl-4-(3-nitrophenyl)-1,4-dihydropyridine-5-carboxylate and after adding to the solution 0.2 g. of a 50% oil dispersion of sodium hydride, the mixture was stirred for 30 minutes at room temperature. After cooling the mixture to −10° C., 0.5 ml. of chloromethoxyethane was added thereto, the temperature of the mixture was elevated to room temperature over a period of about 20 minutes, and after 15 minutes the mixture was cooled again to −10° C. Then, after adding to the reaction product 0.5 ml. of glacial acetic acid and 20 ml. of water, the product was extracted three times each time with 5 ml. of ether. The extracts were combined, washed with 5 ml. of saturated aqueous sodium bicarbonate solution, dried over anhydrous sodium sulfate, and then ether was distilled away. The residue formed was subjected to a silica gel column chromatography, using a 10 : 1 benzene-acetone mixed solvent as an eluant, the effluent was examined by a thin layer chromatography, and then the effluent of the main fraction was concentrated. By recrystallizing the residue thus obtained from a 10 : 1 benzene-hexane mixed solvent, 0.45 g. of faint yellow acicular crystals of ethyl 3-acetyl-1-ethoxymethyl-2,6-dimethyl-4-(3-nitrophenyl)-1,4-dihydropyridine-5-carboxylate melting at 110°–111° C. were obtained.

Elemental analysis for $C_{21}H_{26}N_2O_6$:

| | C(%) | H(%) | N(%) |
|---|---|---|---|
| Calculated: | 61.67 | 6.51 | 6.96 |
| Found: | 62.71 | 6.53 | 6.90 |

EXAMPLES 33–36

By following the same procedure as in Example 32, the novel compounds of this invention shown in the following table were prepared. In the table, R¹, R², R³, and R⁴ of the starting material (I) and the reactant (II) were the same as those of the desired products corresponding to them.

Table

| Ex. No. | Amount of starting material (I) (g) | Reactant (II) X | Amount (ml) | R¹ | R² | Aimed product (III)* R³ | R⁴ | R⁶ | A | n | m |
|---|---|---|---|---|---|---|---|---|---|---|---|
| 33 | 0.5 | Cl | 0.5 | —CH₃ | —CH₃ | —OCH₂CH₃ | —CH₃ | —CH₃ | 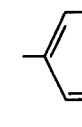 | 0 | 1 |
| 34 | 0.5 | Cl | 0.5 | —CH₃ | —CH₃ | —CH₃ | —CH₃ | —CH₂CH₃ | 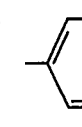 | 0 | 1 |

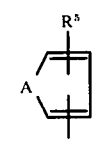

Table-continued

| | | | | | | | | | | |
|---|---|---|---|---|---|---|---|---|---|---|
| 35 | 0.5 | Cl | 0.5 | —CH₂CH₂CH₂— | —OCH₂CH₃ | —CH₃ | —CH₂CH₃ | 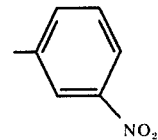 | 0 | 1 |
| 36 | 0.5 | Cl | 0.5 | —CH₂CH₂CH₂— | —OCH₂CH₃ | —CH₃ | —CH₃ | 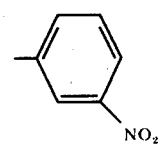 | 0 | 1 |

| Ex. No. | Yield (g) | m.p. (° C) | Elemental analysis | | | | | | Note |
|---|---|---|---|---|---|---|---|---|---|
| | | | Calculated | | | Found | | | |
| | | | C(%) | H(%) | N(%) | C(%) | H(%) | N(%) | |
| 33 | 0.4 | 70 | 61.85 | 6.23 | 7.21 | 61.66 | 6.27 | 7.18 | |
| 34 | 0.35 | 99–101 | 64.50 | 6.50 | 7.52 | 64.40 | 5.56 | 7.53 | Solvent for elution is chloroform |
| 35 | 0.3 | 117 | 63.76 | 6.32 | 6.76 | 63.75 | 6.31 | 6.74 | Reaction solvent is a mixture of 10 ml. of tetrahydrofuran and 0.5 ml. of dimethylformamide |
| 36 | 0.4 | 111 | 62.99 | 6.04 | 7.00 | 62.82 | 6.10 | 6.97 | |

*In these aimed products B is all —CH₂—

EXAMPLE 37

In 10 ml. of dimethylformamide was suspended 0.5 g. of 9-(3-nitrophenyl)-1,8-dioxo-1,2,3,4,5,6,7,8,9,10-decahydroacridine and after adding to the suspension 0.2 g. of a 50% oil dispersion of sodium hydride, the mixture was stirred for 1.5 hours at room temperature. After cooling the mixture to −10° C., 0.5 ml. of chloromethoxyethane was added thereto, the temperature of the mixture was elevated to room temperature over a period of about 20 minutes, stirred for 2 hours and the mixture was cooled again to −10° C. Then, after adding to the reaction product 0.5 ml. of glacial acetic acid and 20 ml. of water, the product was extracted three times each time with 5 ml. of ether. The extracts were combined, washed with 5 ml. of saturated aqueous sodium bicarbonate solution, dried over anhydrous sodium sulfate, and then ether was distilled away. The residue became crystallized by the addition of 5 ml. of ethanol. The crystals were filtered, dissolved in 2 ml. of chloroform and recrystallized by the addition of ethanol and 0.4 g. of pale brown prismatic crystals of 10-ethoxymethyl-9-(3-nitrophenyl)-1,8-dioxo-1,2,3,4,5,6,7,8,9,10-decahydroacridine melting at 222° C. were obtained.

| Elemental analysis for $C_{22}H_{24}N_2O_5$: | | | |
|---|---|---|---|
| | C(%) | H(%) | N(%) |
| Calculated: | 66.65 | 6.10 | 7.07 |
| Found: | 65.89 | 6.14 | 7.17 |

EXAMPLE 38

In 10 ml. of tetrahydrofuran was dissolved 1.0 g. of diethyl 2,6-dimethyl-4-(3-nitrophenyl)-1,4-dihydropyridine-3,5-dicarboxylate and after adding to the solution 0.2 g. of a 50% oil dispersion of sodium hydride, the mixture was stirred for 30 minutes at room temperature. After cooling the mixture to −10° C., 0.5 ml. of 3-chloromethoxy-1-propene was added thereto, the temperature was elevated to room temperature over a period of about 20 minutes, and then after 15 minutes the mixture was cooled again to −10° C. After adding to the reaction product 0.5 ml. of glacial acetic acid and 20 ml. of water, the product was extracted three times each time with 5 ml. of ether at room temperature. The extracts were combined, washed with 5 ml. of saturated aqueous sodium bicarbonate solution, dried over anhydrous sodium sulfate, and then ether was distilled away. The residue was subjected to a silica gel column chromatography using benzene as an eluant. The effluent was then subjected to a thin layer chromatography, and then the effluent or the main fraction was concentrated to provide a white crystalline material. By recrystallizing the crystals from benzene-hexane, 0.74 g. of diethyl 1-allyloxymethyl-2,6-dimethyl-4-(3-nitrophenyl)-1,4-dihydropyridine-3,5-dicarboxylate melting at 111°–112° C. were obtained.

| Elemental analysis for $C_{23}H_{28}N_2O_7$: | | | |
|---|---|---|---|
| | C(%) | H(%) | N(%) |
| Calculated | 62.15 | 6.35 | 6.30 |
| Found: | 62.12 | 6.50 | 6.37 |

EXAMPLE 39 (Tablet)

| | |
|---|---|
| Diethyl 1-ethoxymethyl-2,6-dimethyl-4-(3-nitrophenyl)-1,4-dihydropyridine-3,5-dicarboxylate | 1.0 g. |
| Lactose | 10.0 g. |
| Starch | 3.5 g. |
| Talc | 0.5 g. |

From the formula, 100 tablets were prepared. The tablets had a diameter of 7 mm. and if necessary, the tablets may be coated.

EXAMPLE 40 (Injection)

| | |
|---|---|
| Diethyl 1-ethoxyethyl-2,6-dimethyl-4-(3-nitrophenyl)-1,4-dihydropyridine-3,5-dicarboxylate | 100 mg. |
| Triglyceryl polyoxyethylene (60) | |

| | |
|---|---|
| oxystearate | 12.0 g. |
| Propylene glycol | 10.0 g. |
| Water to make | 100 ml. |

From the formula 100 injection ampules each containing 1 ml. were prepared. The injection was prepared by dissolving the components in water, sterilizing by filtration, and pouring the solution in a one ml. ampule followed by sealing.

EXAMPLE 41

In 160 ml of tetrahydrofuran was dissolved 40 g of diethyl 2,6-dimethyl-4-(3-nitrophenyl)-1,4-dihydropyridine-3,5-dicarboxylate and after adding to the solution 5.2 g of 50% oil dispersion of sodium hydride at room temperature, the resultant mixture was stirred for 30 minutes at room temperature. Then, the mixture was cooled to temperatures of from −10° C. to −20° C., and after adding dropwise thereto a solution of 20 g ethylene sulfate in 80 ml of tetrahydrofuran, the mixture was stirred for 1 hr. at −10° C., and the temperature of the system was raised gradually till room temperature. After further adding 4.0 g of 50% oil dispersion of sodium hydride, the mixture was stirred for 3 hrs. at room temperature. The reaction mixture was cooled to −10° C., and after adding dropwise a solution of 5.0 g ethylene sulfate in 10 ml of tetrahydrofuran, the mixture was stirred for 1 hr. at the same temperature. The reaction mixture was cooled and 800 ml of ether was added thereto and further 100 ml of water was added. The separated aqueous layer was subjected to a silica gel column chromatrography (12 cm× 5.0 cm). After eluting the small amount of raw material using 50 ml of ethyl acetate as an elute, the product was then developed by using 1 : 1 ethyl acetate-methanol mixed solvent as an elute. The solvent of the effluent was distilled away under reduced pressure, and to the residue obtained was added 30 ml of water and after cooling, the crystal formed was filtered to provide 35 g of sodium β-[2,6-dimethyl-3,5-bis(ethoxycarbonyl)-4-(3-nitrophenyl)-1,4-dihydropyridine-1-yl]-ethyl sulfate. By recrystallizing this product from water, scale-shaped yellow crystal was obtained.

| Elemental analysis as $C_{21}H_{25}N_2O_{10}SNa$: | | |
|---|---|---|
| C(%) | H(%) | N(%) |
| Calculated: 48.65 | 4.84 | 5.38 |
| Found: 48.41 | 4.69 | 5.27 |

Nuclear magnetic resonance spectra (CDCl$_3$): signal of 6.0 PPM of raw material (1H, S, proton at 1-position) vanished.

EXAMPLE 42

In 5 ml of tetrahydrofuran was dissolved 1.12 g of diethyl 2,6-dimethyl-4-(3-nitrophenyl)-1,4-dihydropyridine-3,5-dicarboxylate and after adding to the solution 0.17 g of 50% oil dispersion of sodium hydride at room temperature, the resultant mixture was stirred for 30 minutes at room temperature. Then, the mixture was cooled to −30° C., and after adding dropwise thereto 0.74 g of 1,3-propansultone, the temperature of the system was raised till room temperature and the reaction mixture was stirred for 3 days at room temperature. The reaction solution was concentrated and the precipitate formed was washed with 30 ml of ether. This precipitate was dissolved in 2 ml of water and the solution obtained was subjected to a silica gel (30 g) column chromatography. After eluting the small amount of raw material using ethyl acetate as an elute, the product was then developed by using 1 : 1 ethyl acetatemethanol mixed solvent as an elute and the solvent of the effluent was distilled away under reduced pressure. To the residue obtained was added 2 ml of water and after cooling, the crystal formed was filtered to provide 0.35 g of sodium α-[2,6-dimethyl-3,5-bis(ethoxycarbonyl)-4-(3-nitrophenyl)-1,4-dihydropyridin-1-yl] propylsulfonate.

| Elemental analysis as $C_{22}H_{27}N_2SO_9Na$ | | |
|---|---|---|
| C(%) | H(%) | N(%) |
| Calculated: 50.96 | 5.25 | 5.40 |
| Found: 50.69 | 5.30 | 5.15 |

Nuclear magnetic resonance (CDCl$_3$): signal of 6.0 PPM of raw material (1H, S, proton at 1-position) vanished.

EXAMPLE 43

A mixture of 14 g of glycine ethyl ester.hydrochloride, 26 g of ethyl acetoacetate, 15 g of m-nitrobenzaldehyde, 8 g of pyridine and 50 ml of ethanol was refluxed for 30 hrs. under heating and then ethanol of the reaction mixture was distilled away under reduced pressure. The residue was dissolved in 60 ml of chloroform and the solution obtained was washed twice each time with 30 ml of water and dried over anhydrous sodium sulfate, and chloroform of the solution was distilled away under reduced pressure. By adding cold ethanol to the oily residue thus formed, the crystal formed. By recrystallizing this product from ethanol, colorless acicular crystal of ethyl α-[3,5-bis(ethoxycarbonyl)-2,6-dimethyl-4-(3'-nitrophenyl)-1,4-dihydro-1-pyridinyl]acetate melted at 115°–117° C. was obtained (yield : 57%).

EXAMPLE 44

A mixture of 2.4 g of ethyl α-[3,5-bis(ethoxycarbonyl)-2,6-dimethyl-4-(3'-nitrophenyl)-1,4-dihydro-1-pyridinyl]acetate, 10 ml of ethanol and 10 ml of 1N aqueous sodium hydroxide solution was refluxed for 3 hrs. The solvent of the reaction mixture was distilled away and to the residue obtained water was added until the total volume of the solution became 20 ml and the solution formed was washed with benzene. After acidifying the aqueous layer with hydrochloric acid, the oily product precipitated was extracted with chloroform. The solvent of the extracts was distilled away under reduced pressure and the solid residue thus obtained was recrystallized from toluene to provide 1.5 g of the faint yellow prism crystal of α-[3,5-bis(ethoxycarbonyl)-2,6-dimethyl-4-(3'-nitrophenyl)-1,4-dihydro1-pyridinyl] acetic acid melted at 125°–127° C.

| Elemental analysis as $C_{21}H_{24}N_2O_8$ | | |
|---|---|---|
| C(%) | H(%) | N(%) |
| Calculated: 58.33 | 5.59 | 6.48 |
| Found: 58.24 | 5.50 | 6.33 |

This product was suspended in water and after neutralizing the mixture with sodium hydrogen carbonate, the solvent of the mixture was distilled away and the residue obtained was dissolved in hot ethanol. To the solution was added n-hexane for precipitating and greyish powder of sodium α-[3,5-bis(ethoxycarbonyl)-2,6-dimethyl-4-(3'-nitrophenyl)-1,4-dihydro-1-pyridinyl]acetate melted above 230° C. was obtained. This product was easily soluble in water.

| Elemental analysis as $C_{21}H_{23}N_2O_nNa$ | | | | |
|---|---|---|---|---|
| | C(%) | H(%) | N(%) | Na(%) |
| Calculated: | 55.51 | 5.10 | 6.16 | 5.06 |
| Found: | 55.47 | 5.16 | 6.07 | 5.11 |

What is claimed is:
1. The compound, sodium β-[2,6-dimethyl-3,5-bis(ethoxycarbonyl)-4-(3-nitrophenyl)-1,4-dihydropyridine-1-yl]ethyl sulfate.

* * * * *

UNITED STATES PATENT OFFICE
CERTIFICATE OF CORRECTION

Patent No. 4,021,434     Dated May 3, 1977

Inventor(s) Masuo Murakami, et al

It is certified that error appears in the above-identified patent and that said Letters Patent are hereby corrected as shown below:

In the Title Page, in the Title, line 3: "BONAL" should read --BONYL--.

In the Title Page, under "Related U.S. Application Data", line 1: "May 5," should read -- March 19, --.

In Column 1, line 3: "ETHOXYCARBONAL" should read -- ETHOXYCARBONYL --.

Signed and Sealed this

Twenty-ninth Day of November 1977

[SEAL]

Attest:

RUTH C. MASON         LUTRELLE F. PARKER
*Attesting Officer*     *Acting Commissioner of Patents and Trademarks*